United States Patent [19]

Fender et al.

[11] 4,131,113

[45] Dec. 26, 1978

[54] ERG ANALYSIS SYSTEM

[75] Inventors: Derek H. Fender, Altadena; Arthur J. Koblasz, Sierra Madre, both of Calif.

[73] Assignee: California Institute of Technology, Pasadena, Calif.

[21] Appl. No.: 716,025

[22] Filed: Aug. 19, 1976

[51] Int. Cl.² ............................................. A61B 3/00
[52] U.S. Cl. .................................................... 128/2 T
[58] Field of Search ................... 128/2 N, 2 T, 2.1 R, 128/2.1 B; 351/6

[56] References Cited

U.S. PATENT DOCUMENTS

| 3,087,487 | 3/1961 | Clynes | 128/2.1 |
| 3,147,373 | 9/1964 | Clynes | 128/2.1 R |

OTHER PUBLICATIONS

"The Electroretinogram," John Armington, Academy Press, N.Y., 1974, pp. 34–38, 85–90.
"Biological Systems Transfer Function Extraction using Swept Frequency Techniques," Williams et al., Med. & Biol. Engr., vol. 10, 9/72 pp. 609–620.
"Electrical Response of the Human Eye to Sinusoidal Light-Stimulation," A. Troelstra et al., IEEE Trans. Biomed. Engr., 22(5), pp. 369–378, Sep. 1975.
"White Noise Analysis of a Neuron Chain: An Application of the Wiener Theory," by Marmorelis et al., Science, vol. 175, pp. 1276–1278, 1972.

Primary Examiner—Robert W. Michell
Assistant Examiner—Francis J. Jaworski
Attorney, Agent, or Firm—Freilich, Hornbaker, Wasserman, Rosen & Fernandez

[57] ABSTRACT

A method and means is provided for examining the human eye for determining the existence of medical problems by an analysis of electrical signals generated by the retina of an eye in response to a quasi-random light stimulus.

10 Claims, 5 Drawing Figures

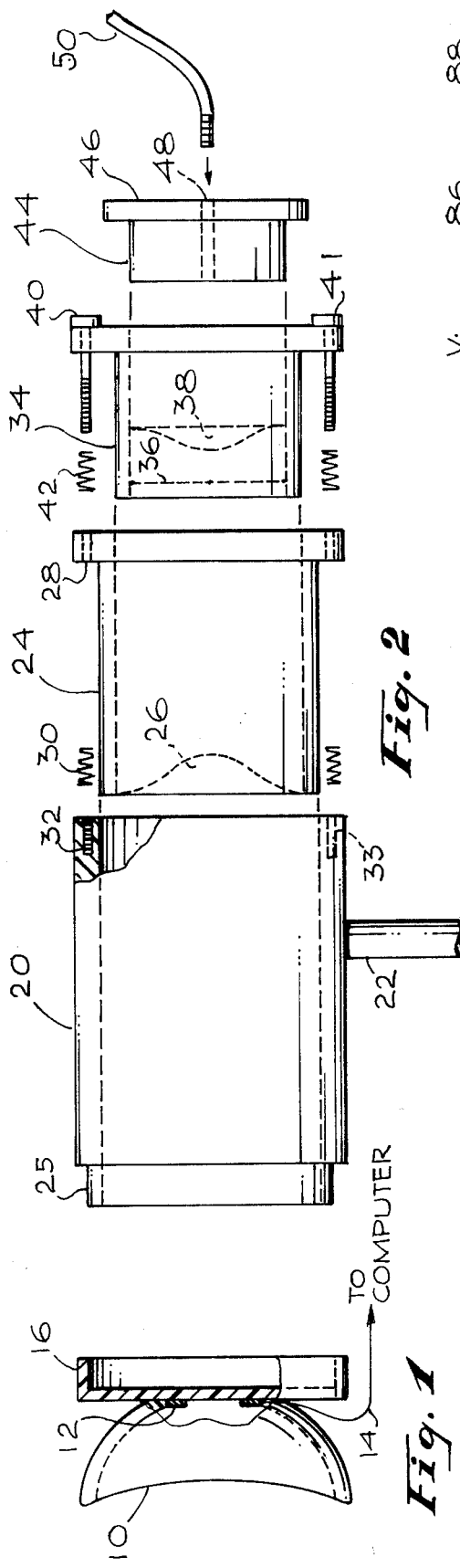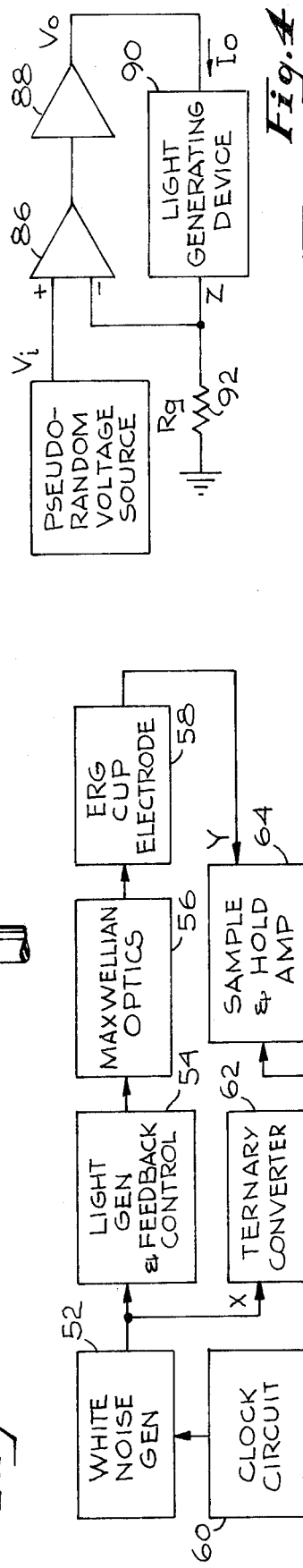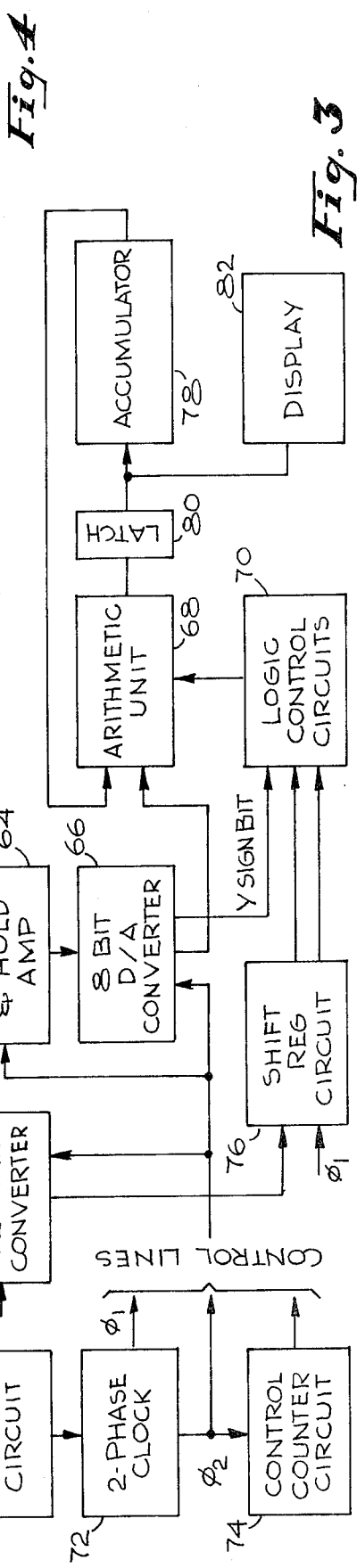

ERG ANALYSIS SYSTEM

ORIGIN OF INVENTION

The invention described herein was made in the course of work under a grant or award from the Department of Health, Education and Welfare.

BACKGROUND OF THE INVENTION

This invention relates to a method and means for analyzing the electroretinogram (ERG) response of the eye to a quasi-random light stimulus.

The fact that the eye provides an electrical response upon illumination is quite well known. It has been demonstrated by connecting two non-polarizable electrodes, one placed over the cornea of the eye and the other on a nearby region of the skin to a suitable detector. Attempts have been made to use this phenomenon for studying retinal functions and for diagnosing retinal diseases.

The usual technique for obtaining a corneal contact is to use a large contact lens with an electrode buried therein. This is uncomfortable for the subject, which tends to increase the noise levels resulting from blinks and eye movements.

Aside from the apparatus problem as indicated above, the retina is a non-linear biological system and a diagnosis of a non-linear system is difficult, especially in real time. In 1958, Norbert Wiener produced a general theory of non-linear system analysis and synthesis. This theory assumes only time-invariance and finite memory; and therefore is applicable to many physical and living systems. Wiener proposed that a non-linear system could be identified by its response to a Gaussian white-noise stimulus, since with such an input the system is tested effectively with all possible inputs (in practice, with a great variety of inputs depending upon the length of the experiment and bandwidth of the stimulus). Wiener's original formulation was not practical for experimental applications, but Lee and Schetzen in 1965, proposed a simpler formulation in terms of cross-correlations between the stimulus and the response. This modification of the Wiener technique provided a feasible approach to analyzing time-invariant, finite memory systems.

Wiener derived the following functional expansion to define the response y to a Gaussian white-noise input x:

$$y(t) = h_o + \int_o^\infty h_1(\tau) \times (t-\tau) d\tau$$
$$+ \int_o^\infty \int h_2(\tau_1,\tau_2) \times (t-\tau_1) \times (t-\tau_2) d\tau_1 d\tau_2 - P \int_o^\infty h_2(\tau,\tau) d\tau$$
$$+ \ldots \text{higher order terms,}$$

where P is the power spectral density of the quasi-random input and by definition is a constant.

The set of kernels ($h_0$, $h_1$, $h_2$, ...) completely characterizes the system. Each kernel $h_n$ is a symmetric function of its arguments. The kernels describe quantitatively the nonlinear cross-talk between different portions of the past of the input as it affects the system response at the present, e.g., how much the response to n different pulses deviates from the superimposed responses to single pulses.

The above-indicated formula $y(t)=F[x(t)]$ indicates a method which is particularly well suited for the study of biological systems. In operation, a stimulus x, is applied to the system, and the output y, is measured. The Wiener formulation demands that the stimulus is a Gaussian white-noise signal which in theory contains all possible stimuli, thus the resulting characterization contains information about the system's response to nearly all stimuli. It can be shown that by multiplying ternary versions of x with values of y the $h_0$, $h_1$ and $h_2$ Wiener kernels can be approximated quite closely.

In an application Ser. No. 715,703, filed Aug. 19, 1976, entitled "System for Computing Weiner Kernels" by Koblasz et al., which is assigned to a common assignee, there is described a computer for solving the indicated equations for first and secondorder kernels. Thus, with the provision of a computer which can be used for diagnosing a nonlinear system, there still remains the problems of accurately measuring the human ERG signals in a manner which is comfortable for the subject and applying these signals to the computer.

OBJECTS AND SUMMARY OF THE INVENTION

It is an object of this invention to provide a method and means for applying quasi-random signals to the human eye, deriving the ERG signals therefrom, and cross-correlating the input to the eye and the ERG output whereby a diagnosis of the retinal conditions may be made.

Another object of this invention is to provide a novel and useful method and means for diagnosis of the retinal conditions from ERG signals.

Still another object of this invention is the provision of a method and means which, in real time and economically, can provide an analysis of the ERG signals derived from a human eye.

The foregoing and other objects of the invention may be achieved in an arrangement wherein band-limited white-noise light intensity signals, which may hereafter be called x signals, are projected into the human eye through a novel ERG cup electrode. This cup electrode comprises a translucent cup adapted to cover the eye. The cup is filled with a suitable conductive fluid which is harmless, such as artificial tear fluid. An annular metal electrode is placed at the base of the cup so that the light stimulus can reach the eye through the center of the annular electrode. The electrolytic tear fluid maintains electrical contact between the front of the eye and the electrode. The signals measured by this electrode can be referenced to signals measured by a disk electrode placed upon an area of the skin adjacent to the eye or to signals measured by another cup electrode positioned over the other eye.

Quasi-random light stimuli termed band-limited white-noise signals, are applied to the eye through the center of the annular electrode. The ERG signals which result, hereafter termed y signals are applied to a computer which is described and shown in the aforesaid copending application. This computer can perform multi-order cross-correlations between the input signals, x and the output signals, y and solve for the kernels, $h_1$, and $h_2$.

By the foregoing technique, because cross-correlation techniques are used in estimating the kernels, the effects of many types of contaminating noise sources are eliminated, e.g., large levels of uncorrelated noise at the output. Further, the quasi-random method of testing provides a very high information rate about the stimulus-response behavior of the eye over the limited period of time that is usually available for testing. Also the use of the quasi-random stimulus does not require a very high luminance level, as a matter of fact the stimulus has a pleasant twinkling effect. This is to be contrasted with the painfully large light flashes which are usually used in clinical situations. Finally, the analysis is performed in real time thus effectively permitting testing to occur in real time.

The novel features of the invention are set forth with particularity in the appended claims. The invention will best be understood from the following description when read in conjunction with the accompanying drawings.

BRIEF DESCRIPTION OF THE DRAWINGS

FIG. 1 is a schematic drawing in section of an ERG cup electrode in accordance with this invention.

FIG. 2 is a cross-sectional view of a light stimulator attachment which may be applied to the ERG cup electrode, in accordance with this invention.

FIG. 3 is a block diagram of an ERG analysis system in accordance with this invention.

FIG. 4 is a block schematic diagram of a voltage to current converting system, which may be used for applying the output of the quasi-random voltage source to the light generating device.

DESCRIPTION OF THE PREFERRED EMBODIMENTS

Figure 5:
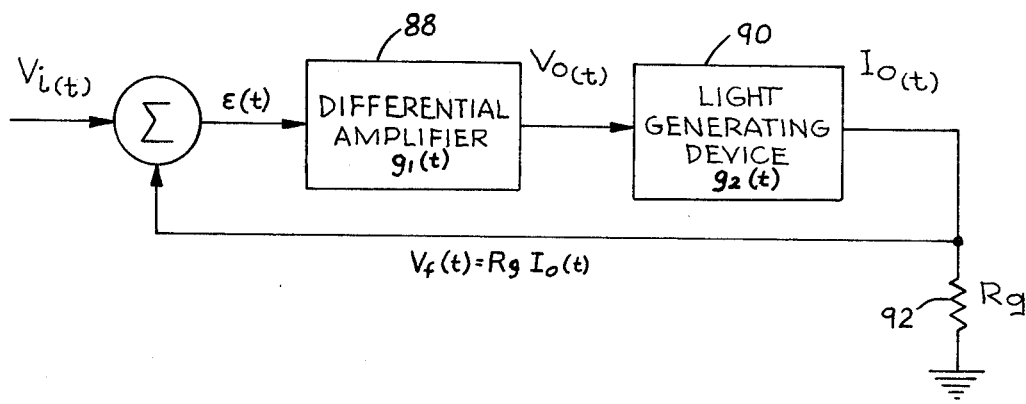
FIG. 5 is a functional drawing of FIG. 4.

FIG. 1 is a view in cross section of an ERG cup electrode which is employed in accordance with this invention. The cup 10 may be made of a translucent plastic material. It may be made in a range of sizes suitable for covering the eye of either an adult subject or a child. An annular shaped electrode 12 is attached to the base of the cup whereby light can pass through the center of the electrode to the eye. The annular shape of this electrode also serves to reduce other noises which can occur. A lead 14 extends from this electrode to an isolated amplifier. The amplifier signal then passes to the computer which will be described in more detail subsequently herein.

A second electrode, not shown, may be placed on the skin at a region near the eye or another cup electrode can be positioned over the other eye to serve as the reference electrode. The base of the ERG cup may be attached to a coupling device 16 which is also translucent. The coupling device is an option which may be omitted but may be used if it is desired to couple the ERG cup to a Maxwellian stimulator, which is shown in FIG. 2.

The cup is filled with an artificial tear fluid during the testing of the eye. The subject applies the cup to his eye dipping his eye into the fluid and observes the light stimulus shown through the center of the annular electrode. Since the artificial tear fluid is electrolytic, the electrode 12 maintains electrical contact with the front of the eye and the retina. Since nothing touches the subject's eye except the artificial tear fluid, the test does not constitute a painful experience which is unlike what occurs with other ERG electrode devices.

FIG. 2 is a cross sectional exploded view of the Maxwellian stimulator. A hollow holder 20 has a handle 22 on the side for holding up the stimulator and is hollow to contain the other parts of the stimulator. One end 25 of the holder 20 engages the attachment on the base of the eye cup so that the stimulator and eye cup are maintained in a fixed relationship. A first lens holder 24 holds an aspheric lens 26, which may be replaced by Opal glass for a diffuse (rather than Maxwellian) view of the stimulus. This lens holder fits within the cylindrical cavity of the holder 20 and is attached thereto by screws 40, 41. Each of the screws passes through a suitable opening 28 and through a spring 30 and thereafter engages a threaded hole such as 32, 33 in the holder 20.

A lens and target holder 34 fits into the hollow opening of the lens holder 24. The lens and target holder 34 has a target 36, supported at the perimeter which is in the shape of an annulus with a cross hair suspended thereacross. The lens 38 is an aspheric lens. The lens and target holder 34 may be attached to the lens holder 24 also by means of the screws 40, which pass through spring 14 and thereafter are threaded into the holes 32, 33 in the lens holder 20.

Finally a cap 44 fits into the cylindrical cavity of the lens and target holder 34. The cap 34 has one end 46 closed except for an opening 48, into which the end of a fiber optic 50, or a light emitting diode, not shown, may be inserted.

The fiber optic transmits the light stimulus to the optics package and therethrough to the eye. The aspheric lens 38 collimates the fiber optic or LED image. The target 36 collimating lens 38, and fiber optic or LED can be moved together by turning the screws 40, 41. The lens 26 functions as a Maxwellian lens. If replaced by Opal glass, a diffuse view (rather than Maxwellian view) of the light stimulus can be provided.

The target configuration enables the subject to maintain his eye fixation very well for Maxwellian viewing. The use of the fiber optic permits electrical and mechanical isolation. Also, since it is coherent it can be used to transmit alignment information in the opposite direction.

In use, the assembled Maxwellian light stimulator and ERG cup are assembled and may be supported to permit a person to press his eye against the cup to bring the eye in contact with the artificial tear fluid with which it is filled.

FIG. 3 is a block diagram of an ERG analysis system, in accordance with this invention. This system will include a band-limited white-noise generator 52 which generates the appropriate voltage signals. Apparatus for producing white-noise signals is described in an article by Don Lancaster published in Radio-Electronics Magazine, in April, 1975, pp. 42-49, and entitled, "Understanding Pseudo-Random Circuits". These are applied to a light generator and feed back control arrangement 54. This arrangement is shown in more detail in FIG. 4.

The output of the light generator and feedback control 54 are applied to the Maxwellian optic arrangement 56 which has been shown in FIG. 2. The light output of the Maxwellian optics 56 is applied to the ERG cup electrode 58, and therethrough to the eye of the subject.

Output signals derived from the ERG cup electrode and the associated reference electrode, as well as output signals from the white-noise generator, are applied to a kernel computer which calculates the $h_1$ and $h_2$ kernels. The remainder of the diagrams shown in FIG. 3 is a block diagram substantially identical with the block diagram of FIG. 1 of the aforesaid copending application. The block schematic diagram comprising the kernel computer in FIG. 3 is shown to assist in an understanding of the invention. However, the details thereof will not be explained since they are already shown and described in detail in the indicated application.

Clock signals for actuating the white-noise generator 52 are derived from a clock circuit 60. The voltage output of the white-noise generator, besides being applied to the light generator and feedback control arrangement 54 constitutes "x", or input signals to the system, and are applied to a ternary converter 62, which converts these x input signals into ternary signals. Ternary signals are two bit signals, which, if the input x signal exceeds a predetermined threshold level represent a +sign, and if the input x signals are below a predetermined threshold level represent a —sign. If the input x signals have an amplitude which falls between the plus and minus threshold, then the ternary signal represents 0.

The output of the ERG cup electrode comprises the y signal input to the computer, and is applied to a sample and hold circuit 64. The output of the sample and hold circuit is applied to an 8 bit analog to digital converter 66, whose function it is to covert the y signals to digital signals representing the amplitude of the y signal plus a sign bit which represents the sign of the y signals. The digital signals representing the amplitude of y are applied to an arithmetic unit 68, the y sign bit and the ternary x signals are applied to logic control circuits 70, whose function it is to instruct the arithmetic unit as to whether or not it should add or subtract its inputs or merely transfer one of its inputs to its output without an operation.

The output of the clock circuit 60 is also applied to a two phase clock circuit 72, whose function it is to provide a two phase clock output ($\phi 1, \phi 2$) from a clock signal applied to its input. The $\phi 2$ output of the two phase clock circuit 72 is applied to control counter circuits 74, which are counter circuits whose outputs are used for determining when outputs should be taken from the ternary converter, the sample and hold amplifier as well as the 8 bit A to D converter. The output of the two bit ternary converter is applied to shift register circuits 76 which are actuated in response to $\phi 1$ clock signals. The shift register circuits are first filled with ternary signals. Thereafter, present and past ternary signal values of x are applied from the shift register circuits to the logic control circuits 70 where they are effectively multiplied with the y sign bit to produce an instruction signal which directs the arithmetic unit 68 to add or subtract its inputs or to transfer out one of its inputs without alteration.

One of the arithmetic unit inputs is the digital value of y which is the output of the 8 bit A to D converter, the other input is the output from an accumulator or memory system 78. The output of the arithmetic unit 68 is applied to a latch circuit 80, which holds that output until it is written into the accumulator memory location which previously provided the input to the arithmetic unit. The latch contents are also applied to a display system 82. Each successive output from the arithmeitc unit is entered into the accumulator to be stored and is later fed back to the arithmetic unit for the purpose of being added to the digital value of y or to have a digital value of y subtracted therefrom, or to be transferred out for storage and cycled back to the input again, in accordance with the instruction signals from the logic circuit 70.

The arrangement shown calculates the $h_2$ kernel by multiplying two ternary values of x with the y sign bit to produce an instruction signal for the arithmetic unit 68. The $h_1$ kernel can be also calculated with the arrangements shown by just multiplying one of the ternary x values with the y sign bit to produce an instruction signal for the arithmetic unit. This can be done by making one of two ternary signals outputs from the shift registers always have a positive value.

FIG. 4 is a block schematic diagram of an impedance correcting circuit. Since the light generating system is a current operating device and since the white-noise generator produces a voltage signal, a correction circuit is necessary to account for the impedance of the light generator. The white-noise voltage source 52 shown in FIG. 3 is applied to the non-inverting input of an operational amplifier 86. The output of the operational amplifier 86 is applied to a unit voltage gain amplifier 88, which provides sufficient current gain to drive the light generating device 90. The current that flows through the light generating device is also fed back to the inverting input of the operational amplifier 86. The inverting input of the amplifier 86 is also connected to ground through a low value resistor 92.

FIG. 5 is a functional schematic drawing of FIG. 4 shown to assist in an understanding of the equations that follow. If the voltage from the pseudo-random source is represented by $V_i(t)$ the voltage output from the amplifier 88 is represented by $V_0(t)$, the output current of the light generating devices $I_0(t)$, and the transfer function of the light generating device is represented by $G_2(s)$, which is principally an inductance, while the resistance of the resistor 92 is represented by $R_g$.

Referring to FIG. 5, we have the following equations in the Laplace domain:

$$\Sigma(s) = V_i(s) - V_f(s)$$

$$V_0(s) = E(s)G_1(s)$$

where $G_1(s)$ is the transfer function of the differential amplifier, $$I_0(s) = G_2(s)V_0(s)$$

$$V_f(s) = R_g I_0(s)$$

After some manipulation, this becomes:

$$\frac{I_o(s)}{V_i(s)} = \frac{1}{\frac{1}{G_1 G_2} + R_g}$$

If $G_1 G_2 \gg 1$

Then $\frac{I_o(s)}{V_i(s)} = \frac{1}{R_g}$ $$I_o(s) = \frac{V_i(s)}{R_g}$$

Accordingly, the current to the light generating device, with the feedback arrangement shown, is solely a function of the voltage output of the white-noise voltage source divided by the resistance of the resistor 92 and is not a function of the impedance of the light generating device.

One type of display system which can be used with the embodiment of the invention is what may be termed a gray scale display. In this system, the display system is a cathode ray tube device which is raster scanned in synchronism with the reading of a buffer memory (not shown) containing values of the first and second order kernels. The kernel values are used to modulate the electron beam of the CRT device.

A library of recorded displays can be produced in which each reflects known retinal defects. By comparing the display for a subject with these recorded displays, diagnoses of a medical problem can be made possible. People who use the system can become as familiar with the display as people who read x-rays.

Accordingly, there has been described and shown hereinabove a novel and useful method and means for examining the human eye for determining any medical problems.

We claim:

1. Apparatus for enabling the examination of the eye of a subject for determining the existence of medical problems, comprising:
   means for generating white-noise electrical signals,
   a light source,
   means for modulating said light source with said white-noise electrical signals to produce modulated light,
   means for applying said modulated light to the eye of a subject to cause the generation of ERG signals by the eye in response thereto, including means for correcting for the impedance of the device which converts the band-limited white-noise voltage signals into quasi-random intensity modutions,
   means for deriving said ERG signals from the eye,
   computer means for cross correlating said white noise electrical signals and said ERG signals for producing $h_1$ and $h_2$ kernels representative of the retinal system, and
   means for displaying said $h_1$ and $h_2$ kernels wherefrom the existence of medical problems can be determined.

2. Apparatus as recited in claim 1 wherein said means for correcting for the impedance includes:
   an operational amplifier having an inverting and non-inverting input and an output,
   means connecting the output of said means for generating white-noise voltage signals to said operational amplifier non-inverting input,
   a voltage to current converter having an input converted to the operational amplifier input and an output connected to said light generating device,
   means for applying current flowing through said light source to the inverting input of said operational amplifier,
   a point of reference potential, and
   resistance means connecting said operational amplifier to said point of reference potential.

3. Apparatus for enabling the examination of the eye of a subject for determining the existence of medical problems, comprising:
   means for generating white-noise electrical signals,
   a light source,
   means for modulating said light source with said white-noise electrical signals to produce modulated light,
   means for applying said modulated light to the eye of a subject to cause the generation of ERG signals by the eye in response thereto,
   means for deriving said ERG signals from the eye, including
     a container means having a translucent region for passing light therethrough, said container being large enough to cover the eye of said subject,
     a conductive, translucent fluid in said container for contacting the eye of said subject, and
     a conductor extending from within said container where it contacts said fluid to the exterior of said container,
   computer means for cross correlating said white noise electrical signals and said ERG signals for producing $h_1$ and $h_2$ kernels representative of the retinal system, and
   means for displaying said $h_1$ and $h_2$ kernels wherefrom the existence of medical problems can be determined.

4. Apparatus as recited in claim 3 wherein said conductor within said container is substantially circular in shape and is positioned at said translucent region whereby light can pass through the center of said circularly shaped conductor to the eye.

5. Apparatus as recited in claim 3 wherein said means for applying said modulated light to the eye of a subject includes:
   hollow holder means having one end adapted to be applied to said container means,
   said container means having means to engage said one end of said hollow holder means,
   a hollow lens holder means having a size to fit within said hollow holder means through its other end, and having a flange at one end large enough to prevent complete insertion into said hollow holder means,
   a lens supported at the other end of said hollow lens holder means,
   a hollow lens and target holder means having a size to fit within siad hollow lens holder means through its one end, and having a flange at its other end to prevent complete insertion into said hollow lens holder,
   a target supported at said one end of said hollow lens and target holder,
   a lens supported within said hollow lens and target holder,
   a cap means for enclosing the other end of said hollow lens and target holder having an opening therein for permitting light to pass therethrough, and
   screw means for adjustably holding said hollow lens holder and hollow lens and target holder in aligned engagement with one another and with said hollow holder whereby light applied to the opening in said cap means may reach the eye of the subject.

6. Apparatus for enabling the examination of the eye of a subject for determining the existence of medical problems comprising:
   means for generating white-noise electrical signals,
   a light source,
   means for modulating said light source with said electrical signals to provide modulated light,
   an eye cup having a translucent region therein,
   a conductive transparent fluid within said eye cup to which the eye of said subject is applied,
   conductor means extending from within said eye cup wherein it contacts said fluid, to the outside of said eye cup,
   means for applying said modulated light to said eye cup translucent region whereby the eye will generate ERG signals in response to the light which reaches it through said fluid whereby said conductor means will have the ERG signals applied thereto, computer means to which said white-noise electrical signals and the ERG signals on said conductor means are applied for cross correlating these signals and producing as output $h_1$ and $h_2$ kernels representative of the retinal system, and means for displaying said kernels wherefrom the existence of medical problems may be determined.

7. Apparatus as recited in claim 6 wherein said conductor means within said eye cup has a substantially annular form.

8. Apparatus for deriving electrical signals from the eye of a subject comprising eye cup means for holding a conductive translucent fluid and having a translucent region therein and an electrical conductor within said eye cup means substantially in the form of a ring enclosing said translucent region and extending from within said eye cup means externally therefrom, whereby electrical signals produced by the eye may be detected on said electrical conductor when said eye cup is filled with said conductive translucent fluid which is in contact with the eye of said subject, said apparatus including Maxwellian stimulator means adapted to engage said eye cup means comprising:

hollow holder means having one end adapted to be applied to said eye cup means, said eye cup means having means to engage said one end of said hollow holder means, a hollow lens holder means having a size to fit within said hollow holder means through its other end, and having a flange at one end large enough to prevent complete insertion into said hollow holder means, a lens supported at the other end of said hollow lens holder means, a hollow lens and target holder means having a size to fit within said hollow lens holder means through its one end, and having a flange at its other end to prevent complete insertion into said hollow lens holder, a target supported at said one end of said hollow lens and target holder, a lens supported within said hollow lens and target holder, a cap means for enclosing the other end of said hollow lens and target holder having an opening therein for permitting insertion of fiber optic or LED, and screw means for adjustably holding said hollow lens holder and hollow lens and target holder in aligned engagement with one another and with said hollow holder whereby light image at said cap means may reach the eye of the subject.

9. A method for enabling the examination of the eye of a subject for determining the existence of medical problems comprising:

generating a band-limited white-noise voltage signal, modulating a light source with said white-noise voltage signal to produce the appropriate intensity modulations, applying said modulated light signals to the eye of a subject to cause the generation of ERG signals by the eye in response thereto, deriving said ERG signals from the eye, cross-correlating said white-noise input signals and said ERG signals to produce $h_1$ and $h_2$ kernels representative of said retinal system, and displaying said $h_1$ and $h_2$ kernels wherefrom the existence of retinal function may be determined, including the step of converting said white-noise voltage signal to a ternary signal, where said cross-correlating step is with said ternary signal to produce $h_1$ and $h_2$ kernels.

10. Apparatus for enabling the examination of the eye of a subject for determining the existence of medical problems, comprising:

means for generating white-noise electrical signals, a light source, means for modulating said light source with said white-noise electrical signals to produce modulated light, means for applying said modulated light to the eye of a subject to cause the generation of ERG signals by the eye in response thereto, means for deriving said ERG signals from the eye, computer means for cross correlating said white noise electrical signals and said ERG signals for producing $h_1$ and $h_2$ kernels representative of the retinal system, and means for displaying said $h_1$ and $h_2$ kernels wherefrom the existence of medical problems can be determined, including means for converting said white-noise voltage signal to a ternary signal, where said computer means cross-correlates with said ternary signal to produce $h_1$ and $h_2$ kernels.

* * * * *